United States Patent
Govari et al.

(10) Patent No.: US 11,154,352 B2
(45) Date of Patent: Oct. 26, 2021

(54) POWER CONTROLLED SHORT DURATION ABLATION WITH VARYING TEMPERATURE LIMITS

(71) Applicant: Biosense Webster (Israel) Ltd., Yokneam (IL)

(72) Inventors: Assaf Govari, Haifa (IL); Andres Claudio Altmann, Haifa (IL); Israel Zilberman, Yokneam (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 440 days.

(21) Appl. No.: 16/219,274

(22) Filed: Dec. 13, 2018

(65) Prior Publication Data
US 2019/0223947 A1    Jul. 25, 2019

Related U.S. Application Data

(60) Provisional application No. 62/620,703, filed on Jan. 23, 2018.

(51) Int. Cl.
*A61B 18/14* (2006.01)
*A61B 18/00* (2006.01)
(Continued)

(52) U.S. Cl.
CPC ...... *A61B 18/1492* (2013.01); *A61B 18/1206* (2013.01); *A61N 7/00* (2013.01);
(Continued)

(58) Field of Classification Search
CPC .......... A61B 2018/00773; A61B 2018/00779; A61B 2018/00791; A61B 2018/00797;
(Continued)

(56) References Cited

U.S. PATENT DOCUMENTS 7,674,257 B2 * 3/2010 Pless ................ A61B 17/22012
606/27
2004/0122420 A1    6/2004 Amoah
(Continued)

FOREIGN PATENT DOCUMENTS

EP    2021846 A2    2/2009
EP    3216412 A1    9/2017

OTHER PUBLICATIONS

European Search Report for corresponding EPA No. 19153051.8 dated Jun. 19, 2019.

*Primary Examiner* — Linda C Dvorak
*Assistant Examiner* — Nicholas S Borsch (57) ABSTRACT

Apparatus, consisting of a probe with a temperature sensor and a transducer in contact with a living subject's tissue. A power supply delivers electrical power to the transducer for tissue ablation. A controller receives a signal from the temperature sensor and in response outputs a tissue temperature. During a first time period the power supply delivers no more than a first target power to the transducer, and reduces the power when a first maximum allowable temperature of the tissue is exceeded. During a transition time period the power supply delivers no more than a second target power, while reducing the delivered power when the first maximum allowable temperature of the tissue is exceeded. During a second time period the power supply delivers no more than the second target power, while reducing the delivered power when a second maximum allowable temperature, less than the first maximum allowable temperature, is exceeded.

14 Claims, 5 Drawing Sheets

(51) Int. Cl.
  *A61B 18/12*  (2006.01)
  *A61N 7/00*  (2006.01)
  *A61B 34/20*  (2016.01)
  *A61B 90/00*  (2016.01)
  *A61B 34/00*  (2016.01)

(52) U.S. Cl.
  CPC .............. *A61B 34/20* (2016.02); *A61B 34/25* (2016.02); *A61B 2018/00351* (2013.01); *A61B 2018/00577* (2013.01); *A61B 2018/00648* (2013.01); *A61B 2018/00666* (2013.01); *A61B 2018/00702* (2013.01); *A61B 2018/00714* (2013.01); *A61B 2018/00761* (2013.01); *A61B 2018/00791* (2013.01); *A61B 2018/00797* (2013.01); *A61B 2018/00875* (2013.01); *A61B 2090/065* (2016.02); *A61B 2218/001* (2013.01)

(58) Field of Classification Search
  CPC ........... A61B 2018/00803; A61B 2018/00815; A61B 2018/00821; A61B 2018/00875; A61B 2018/00886; A61B 2018/00702; A61B 2018/00708; A61B 2018/00714; A61B 2018/00755; A61B 2018/00761; A61B 18/1492; A61B 18/1206; A61B 2018/00648; A61B 34/20; A61B 2018/00351; A61B 2090/065; A61B 34/25; A61B 2218/001; A61B 2018/00666; A61B 2018/00577; A61B 18/04; A61N 7/00
  USPC .......................................................... 606/34
  See application file for complete search history.

(56) References Cited

U.S. PATENT DOCUMENTS

| | | |
|---|---|---|
| 2005/0021024 A1 | 1/2005 | Hooven |
| 2006/0224150 A1* | 10/2006 | Arts ....................... A61B 18/16 606/32 |
| 2011/0224573 A1 | 9/2011 | Bar-Tal |
| 2012/0101538 A1 | 4/2012 | Ballakur |
| 2012/0123400 A1 | 5/2012 | Francischelli et al. |
| 2013/0237977 A1* | 9/2013 | McCarthy .......... A61B 18/1206 606/20 |

* cited by examiner

POWER CONTROLLED SHORT DURATION ABLATION WITH VARYING TEMPERATURE LIMITS

CROSS-REFERENCE TO RELATED APPLICATION

This application claims the benefit of U.S. Provisional Patent Application 62/620,703, filed 23 Jan. 2018, which is incorporated herein by reference.

FIELD OF THE INVENTION

This invention relates generally to surgery, and specifically to surgery using radiofrequency ablation.

BACKGROUND OF THE INVENTION

Radiofrequency (RF) ablation is a treatment modality that kills unwanted tissue by heat. Starting with cardiac arrhythmia treatment in the 1980s, RF ablation has found clinical application in a number of diseases, and is now the treatment of choice for certain types of cardiac arrhythmia, and certain cancers. During RF ablation, an electrode on a distal region of a catheter is inserted into proximity with the target region under medical imaging guidance. Tissue surrounding the electrode in the target region is destroyed by heating via RF electric current.

Typically, during an ablation procedure, a maximum allowable temperature measured at the distal region remains fixed, typically in the range of 55° C.-65° C. Some systems referring to temperature are described below.

U.S. Patent Application 2012/0123400, to Francischelli et al., describes a system wherein delivery of ablation energy is ceased at a time based, at least in part, on when at least one of an accumulated effective temperature of the tissue over time exceeds a thermal dose threshold and an accumulated effective energy of the tissue over time exceeds an effective energy threshold.

U.S. Patent Application 2013/0237977, to McCarthy et al., describes a system for temperature-controlled ablation using radiometric feedback.

U.S. Patent Application 2005/0021024, to Hooven, describes apparatus for transmural ablation using an instrument containing first and second jaw member and at least one of the jaw members having an ablation member. A monitoring device measures a suitable parameter, such as impedance or temperature, and indicates when the tissue has been fully ablated.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE DISCLOSURE

An embodiment of the present invention provides apparatus, including:

a probe having a distal end incorporating a temperature sensor and a transducer in contact with tissue in a body of a living subject;

a power supply configured to deliver electrical power to the transducer, so as to ablate the tissue; and a controller, coupled to the power supply and to the probe, and configured:

to receive a signal from the temperature sensor and in response to the signal to output an indication of a temperature of the tissue, during a first time period to activate the power supply to deliver no more than a first target power to the transducer so as to ablate the tissue, and to reduce the electrical power delivered to the transducer when a first maximum allowable temperature of the tissue is exceeded, during a transition time period immediately following the first time period, to activate the power supply to deliver no more than a second target power, less than the first target power, to the transducer so as to ablate the tissue, while reducing the delivered power when the first maximum allowable temperature of the tissue is exceeded, and during a second time period immediately following the transition time period, to activate the power supply to deliver no more than the second target power to the transducer, while reducing the delivered power when a second maximum allowable temperature, less than the first maximum allowable temperature, is exceeded.

Typically the transducer is one of an electrode and an ultrasonic transmitter.

In a disclosed embodiment the electrical power consists of radiofrequency power.

In a further disclosed embodiment the controller is configured to deliver a first actual power less than the first target power in the first time period, and to deliver a second actual power less than the second target power in the transition time period and in the second time period.

In a yet further disclose embodiment the transducer includes an electrode, and the power supply is configured to measure an impedance of the electrode during the first, transition, and second time periods, and to stop delivery of the electrical power if the impedance exceeds a pre-set value.

In an alternative embodiment the first target power is between 70 W and 100 W, and the second target power is between 20 W and 60 W.

In a further alternative embodiment the first time period is between 1 s and 6 s, the transition time period is between 1 s and 2 s, and the second time period is up to 13 s.

There is also provided a method, consisting of:

providing a probe having a distal end having a temperature sensor and a transducer that is configured to contact tissue in a body of a living subject;

delivering electrical power from a power supply to the transducer, so as to ablate the tissue;

receiving a signal from the temperature sensor and in response to the signal outputting an indication of a temperature of the tissue;

during a first time period activating the power supply to deliver no more than a first target power to the transducer so as to ablate the tissue, and reducing the electrical power delivered to the transducer when a first maximum allowable temperature of the tissue is exceeded;

during a transition time period immediately following the first time period, activating the power supply to deliver no more than a second target power, less than the first target power, to the transducer so as to ablate the tissue, while reducing the delivered power when the first maximum allowable temperature of the tissue is exceeded; and during a second time period immediately following the transition time period, activating the power supply to deliver no more than the second target power to the transducer, while reducing the delivered power when a second maximum allowable temperature, less than the first maximum allowable temperature, is exceeded.

The present disclosure will be more fully understood from the following detailed description of the embodiments thereof, taken together with the drawings, in which:

DETAILED DESCRIPTION OF EMBODIMENTS

Overview

Typically, in an RF ablation procedure, an electrode on the distal end of a probe is inserted to contact a target region, and energy is transferred from the electrode to heat and effectively destroy the tissue. During the procedure a maximum allowable temperature of the distal end, and thus of the tissue, is typically kept fixed within bounds, typically 40° C.-65° C.

However, keeping the maximum allowable temperature fixed at one value throughout the whole procedure does not take into account the properties of the tissue being ablated, especially the fact that tissue response vs. temperature is extremely non-linear.

Embodiments of the invention adapt for the non-linear tissue behavior by reducing the maximum allowable temperature during a lower power phase of the ablation. For example, in a first ablation phase of 4 s the target RF power from a generator is 90 W, and the maximum allowable temperature is set at 65° C. The target power is then lowered to 50 W, which is provided for a further 4 s. During the lower power phase the maximum allowable temperature is reduced to 45° C. However, this reduction is not after 4 s, since otherwise the generator would shut down. Rather, the maximum allowable temperature reduction is only implemented a preset transition time period after the target power reduction. Typically, the transition time period is of the order of approximately 1 s, and is set so that an expected measured temperature has already reached its new allowable temperature.

Thus, an embodiment of the present invention comprises a probe, which has a distal end having a temperature sensor and a transducer, typically an electrode, in contact with tissue in a body of a living subject. A power supply delivers power to the transducer, so as to ablate the tissue.

A controller receives a signal from the temperature sensor so as to output an indication of a temperature of the tissue. During a first time period the controller activates the power supply to deliver no more than a first target power to the transducer so as to ablate the tissue, and reduces the electrical power delivered to the transducer when a first maximum allowable temperature of the tissue is exceeded.

During a transition time period immediately following the first time period, the controller activates the power supply to deliver no more than a second target power, less than the first target power, to the transducer so as to ablate the tissue, while reducing the delivered power when the first maximum allowable temperature of the tissue is exceeded.

During a second time period immediately following the transition time period, the controller activates the power supply to deliver no more than the second target power to the transducer, while reducing the delivered power when a second maximum allowable temperature, less than the first maximum allowable temperature, is exceeded.

DETAILED DESCRIPTION

Figure 1:
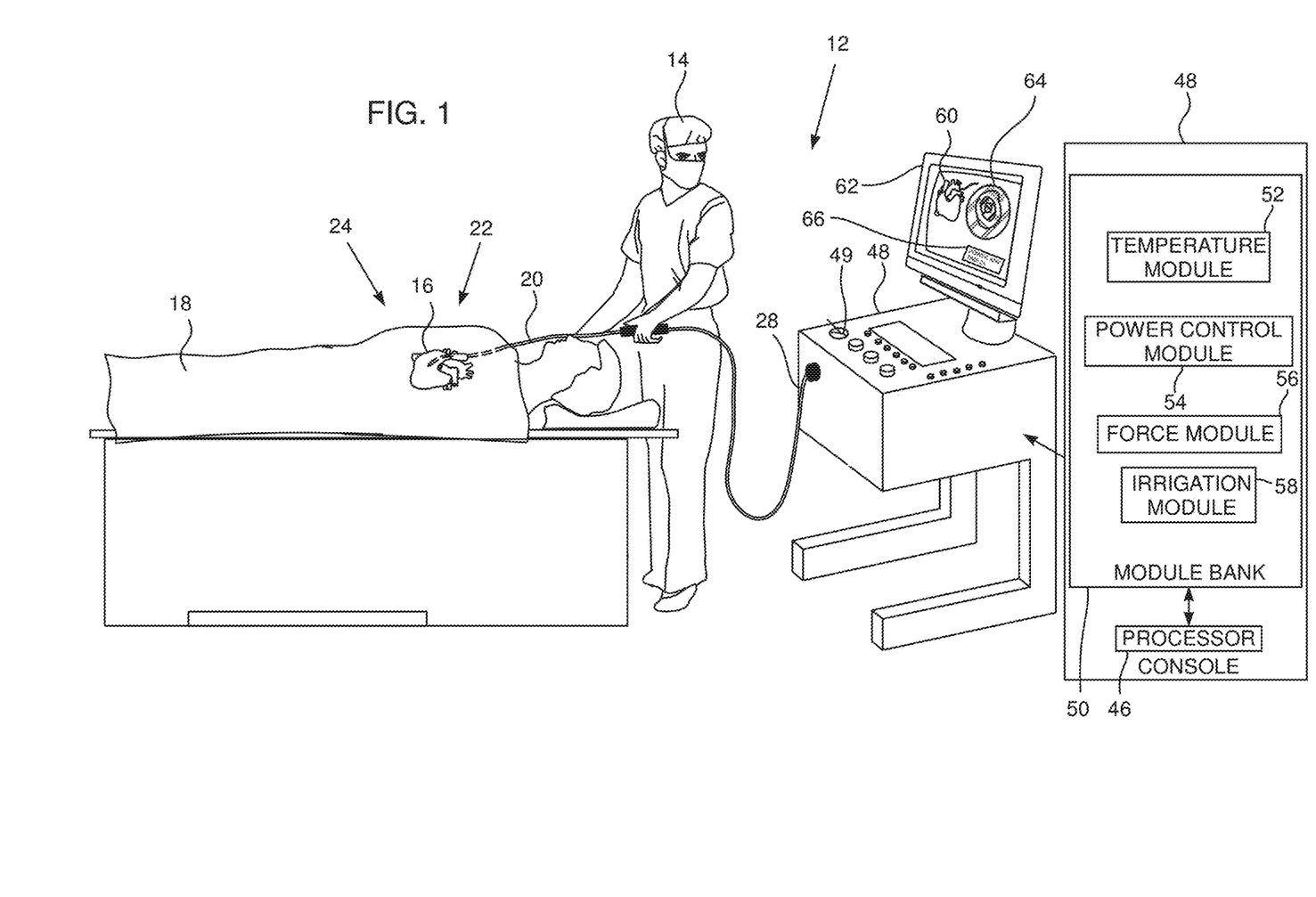
FIG. 1 is a schematic illustration of an invasive medical procedure, according to an embodiment of the present invention.

FIG. 1 is a schematic illustration of an invasive medical procedure using an ablation apparatus 12, according to an embodiment of the present invention. The procedure is performed by a physician 14, and, by way of example, the procedure in the description herein below is assumed to comprise ablation of a portion of a myocardium 16 of the heart of a human patient 18. However, it will be understood that embodiments of the present invention are not just applicable to this specific procedure, and may include substantially any ablation procedure on biological tissue.

In order to perform the ablation, physician 14 inserts a probe 20 into a lumen of the patient, so that a distal end 22 of the probe enters the heart of the patient. Distal end 22 comprises one or more electrodes 24 mounted on the outside of the distal end, the electrodes contacting respective locations of the myocardium. Probe 20 has a proximal end 28. Distal end 22 of the probe is described in more detail below with reference to FIGS. 2A, 2B, 2C and 2D.

Apparatus 12 is controlled by a system processor 46, also referred to herein as controller 46, which is located in an operating console 48 of the apparatus. Console 48 comprises controls 49 which are used by physician 14 to communicate with the processor. During the procedure, controller 46 typically tracks a location and an orientation of distal end 22 of the probe, using any method known in the art. For example, controller 46 may use a magnetic tracking method, wherein magnetic transmitters external to patient 18 generate signals in coils positioned in the distal end. The Carto® system produced by Biosense Webster, of 33 Technology Drive, Irvine, Calif. 92618 USA, uses such a tracking method.

The software for processor 46 may be downloaded to the processor in electronic form, over a network, for example. Alternatively or additionally, the software may be provided on non-transitory tangible media, such as optical, magnetic, or electronic storage media. The track of distal end 22 is typically displayed on a three-dimensional representation 60 of the heart of patient 18 on a screen 62. The progress of the ablation performed with apparatus 12 is typically also displayed on screen 62, as a graphic 64 and/or alphanumeric data 66.

In order to operate apparatus 12, processor 46 communicates with a module bank 50, which has a number of modules used by the processor to operate the apparatus. Thus, module bank 50 comprises a temperature module 52, a power control module 54, a force module 56, and an irrigation module 58, the functions of which are described below. The modules may comprise hardware as well as software elements.

Figure 2A:
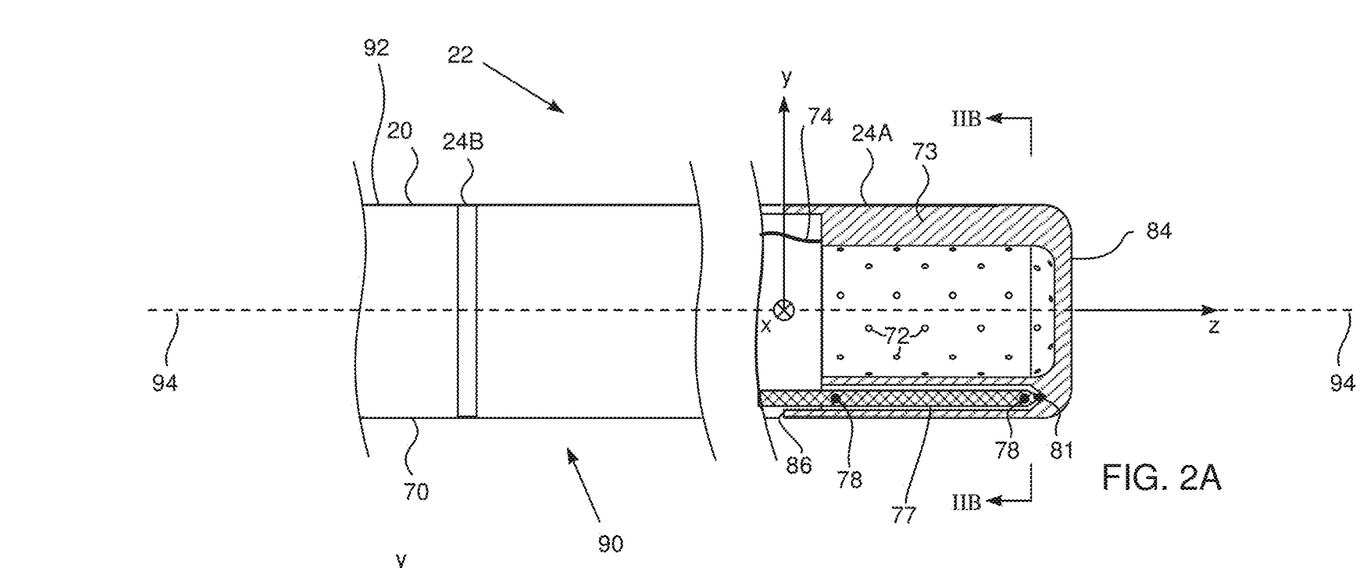
FIGS. 2A, 2B, 2C, and 2D schematically illustrate a distal end of a probe used in the procedure, according to an embodiment of the present invention.
Figure 2B:
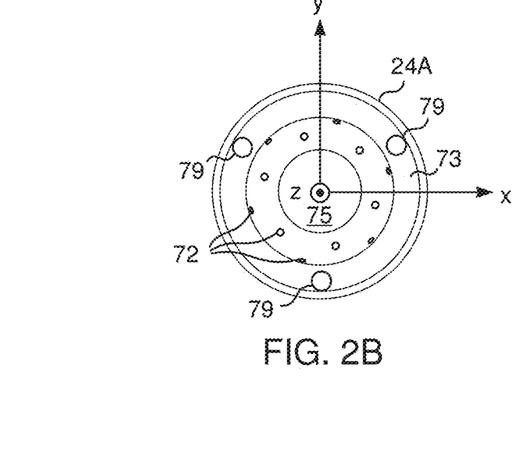
Figure 2C:
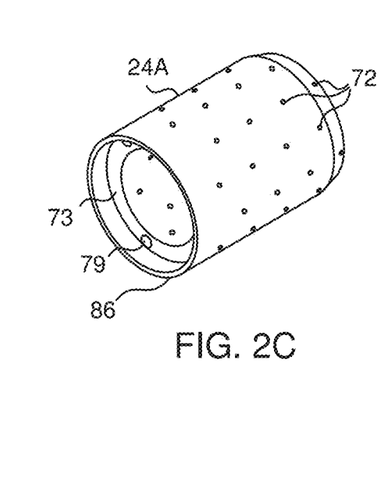
Figure 2D:
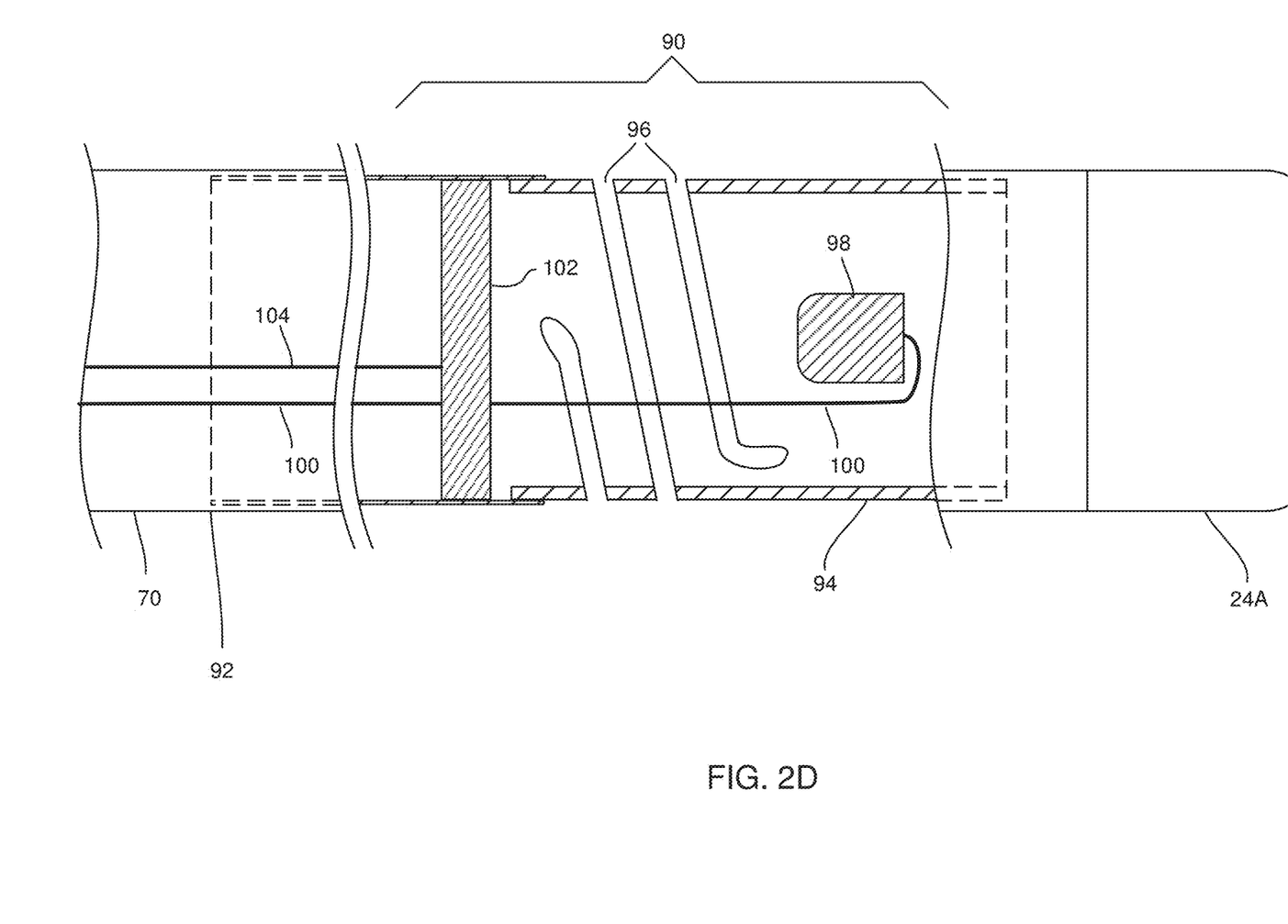

FIGS. 2A, 2B, 2C, and 2D schematically illustrate distal end 22 of probe 20, according to an embodiment of the present invention. FIG. 2A is a sectional view along the length of the probe, FIG. 2B is a cross-sectional view along a cut IIB-IIB that is marked in FIG. 2A, FIG. 2C is a perspective view of a section of the distal end and FIG. 2D is a schematic cross-sectional view of a force sensor 90 incorporated into a proximal portion 92 of the distal end. An insertion tube 70 extends along the length of the probe and is connected at the termination of its distal end to a conductive cap electrode 24A, which is used for ablation. Conductive cap electrode 24A is herein also termed the ablation electrode. Cap electrode 24A has an approximately plane conducting surface 84 at its distal end and a substantially circular edge 86 at its proximal end. Proximal to ablation electrode 24A there are typically other electrodes such as an electrode 24B. Typically, insertion tube 70 comprises a flexible, biocompatible polymer, while electrodes 24A, 24B comprise a biocompatible metal, such as gold or platinum, for example. Ablation electrode 24A is typically perforated by an array of irrigation apertures 72. In one embodiment there are 36 apertures 72, distributed evenly over electrode 24A.

An electrical conductor 74 conveys radio-frequency (RF) electrical energy from power control module 54 (FIG. 1), through insertion tube 70, to electrode 24A, and thus energizes the electrode to ablate myocardial tissue with which the electrode is in contact. Electrode 24A thus acts as an energy transducer, converting electrical energy to heat energy, and is also referred to herein as transducer 24A. As described below, module 54 acts as a power supply and controls the level of RF power dissipated via transducer 24A. Module 54 is also referred to herein as power supply 54. During the ablation procedure, irrigation fluid flowing out through apertures 72 irrigates the tissue under treatment, and the rate of flow of fluid is controlled by irrigation module 58. The irrigation fluid is delivered to transducer 24A by a tube (not shown in the diagram) within insertion tube 70.

Temperature sensors 78 are mounted within conductive cap electrode 24A at locations that are arrayed around the distal tip of the probe, both axially and circumferentially. In a disclosed embodiment considered herein, cap 24A contains six sensors, with one group of three sensors in a distal location, close to the tip, and another group of three sensors in a slightly more proximal location. This distribution is shown only by way of example, however, and greater or smaller numbers of sensors may be mounted in any suitable locations within the cap. Sensors 78 may comprise thermocouples, thermistors, or any other suitable type of miniature temperature sensor. Sensors 78 are connected by leads (not shown in the diagram) running through the length of insertion tube 70 to provide temperature signals to temperature module 52.

In a disclosed embodiment cap 24A comprises a side wall 73 that is relatively thick, on the order of 0.5 mm thick, in order to provide the desired thermal insulation between temperature sensors 78 and the irrigation fluid inside a central cavity 75 of the tip. The irrigation fluid exits cavity 75 through apertures 72. Sensors 78 are mounted on rods 77, which are fitted into longitudinal bores 79 in side wall 73. Rods 77 may comprise a suitable plastic material, such as polyimide, and may be held in place at their distal ends by a suitable glue 81, such as epoxy. U.S. patent application Ser. No. 13/716,578, which is incorporated herein by reference, describes a catheter having temperature sensors mounted in a similar configuration to that described above. The arrangement described above provides an array of six sensors 78, but other arrangements, and other numbers of sensors, will be apparent to those having ordinary skill in the art, and all such arrangements and numbers are included within the scope of the present invention.

In the description herein, distal end 22 is assumed to define a set of xyz orthogonal axes, where an axis 94 of the distal end corresponds to the z axis of the set. For simplicity and by way of example, the y axis is assumed to be in the plane of the paper, the xy plane is herein assumed to correspond to the plane defined by circle 86, and the origin of the xyz axes is assumed to be the center of the circle.

FIG. 2D is a schematic, sectional view of force sensor 90, according to an embodiment of the present invention. Sensor 90 comprises a spring 94, herein assumed to comprise a plurality of helices 96, connecting cap 24A to proximal end 92. A position sensor 98 is fixed to the distal side of spring 94, and is herein assumed to comprise one or more coils coupled by conductors 100 to force module 56.

An RF transmitter 102, typically a coil, is fixed to the proximal side of spring 94, and the RF energy for the transmitter is provided from force module 56 via conductors 104. The RF energy from the transmitter traverses sensor 98, generating a corresponding signal in conductors 100 of the sensor.

In operation, as force is exerted on cap 24A sensor 98 moves relative to transmitter 102, and the movement causes a change in the signals of the sensor. Force module 56 uses the change in signal of the sensor to provide a metric of the force on cap 24A. The metric typically provides the force in magnitude and direction.

A more detailed description of a sensor similar to sensor 90 is provided in U.S. Patent Application 2011/0130648, which is incorporated herein by reference. Furthermore, it will be understood that embodiments of the present invention are not limited to one type of force sensor, so that the scope of the present invention comprises substantially any force sensor known in the art.

Returning to FIG. 1, temperature module 52 receives signals from the six sensors 78 within cap 24A, and uses the signals to determine a maximum value of the six measured temperatures. The temperature module is configured to calculate the maximum temperature at a fixed rate, herein assumed to be every 33 ms, but other embodiments may calculate the maximum temperature at higher or lower rates. In some embodiments the maximum temperature is determined at a frequency of at least 30 Hz. The calculated maximum temperature is herein also termed the measured temperature, and the measured temperature is assumed to correspond to the temperature of the tissue being ablated. The temperature module passes the measured temperature value to power supply 54.

Power supply 54 provides RF power to cap 24A in a range of 1 W to 100 W, and in embodiments of the present invention the power is provided in two time periods, also referred to herein as phases. In an initial phase the module can be configured to provide an initial maximum RF power to cap 24A that can be set within a range of 70 W-100 W. In a subsequent phase, immediately after the initial phase, the module can be configured to provide a subsequent maximum RF power to cap 24A in a different range from the initial maximum. In one embodiment the subsequent maximum power range is 20 W-60 W. The initial maximum RF power and the subsequent maximum RF power are also termed herein the first target power and the second target power.

The initial and subsequent maximum powers, and the time periods for which the different powers are delivered, together with other variable parameters, described below, are selected by physician 14. Physician 14 may typically choose the values of the parameters via preset menus presented to the physician on screen 62. Alternatively, physician 14 may choose the values of the variable parameters individually. The actual power delivered at any time during an ablation procedure is determined by the measured temperature received from temperature module 52, as described below.

Thus, notwithstanding the powers selected by the physician, the power control module is configured to reduce the power delivered, typically by between approximately 5% and approximately 95%, if the measured temperature received from the temperature module reaches or exceeds a maximum allowable temperature. The maximum allowable temperature is set according to the phase of the ablation procedure, and, except as described below, is typically different for each phase. Typically, exceeding the maximum allowable temperature causes undesirable effects such as charring, coagulation on cap 24A, and/or steam pops in the tissue being ablated.

During the initial phase the maximum allowable temperature is set at a first maximum allowable temperature; in one embodiment the first maximum allowable temperature is 65° C. During the subsequent phase, except for a transition time period immediately after the initial phase, the maximum allowable temperature is set at a second maximum allowable temperature; in one embodiment the second maximum allowable temperature is 45° C. During the transition time period, which in one embodiment is 1 second, the maximum allowable temperature remains at the value set for the first maximum allowable temperature.

The power control module also measures an impedance of cap 24A. The impedance is measured at a predefined rate, herein assumed to be every 500 ms, but other embodiments may measure the impedance at a lower or higher rate.

Typically, during an ablation session, the impedance of cap 24A decreases. Embodiments of the present invention also check if the impedance increases from a previous impedance measurement by more than a pre-set value, herein assumed to be 7Ω, although other embodiments may use larger or smaller values of impedance increase for the pre-set value. An increase of impedance typically occurs if there is an unwanted change in the tissue being ablated, such as charring or steam popping. If the impedance increases by more than the pre-set value, the power control module is configured to stop the RF delivery to cap 24A.

As explained above, force module 56 is able to measure the force on cap 24A. In an embodiment, the allowable force for an ablation is in the range of 5 g-50 g.

Irrigation module 58 governs the rate at which irrigation fluid is delivered to the catheter tip. In some embodiments of the present invention it may be set within the range of 8-45 ml/min.

Figure 3:
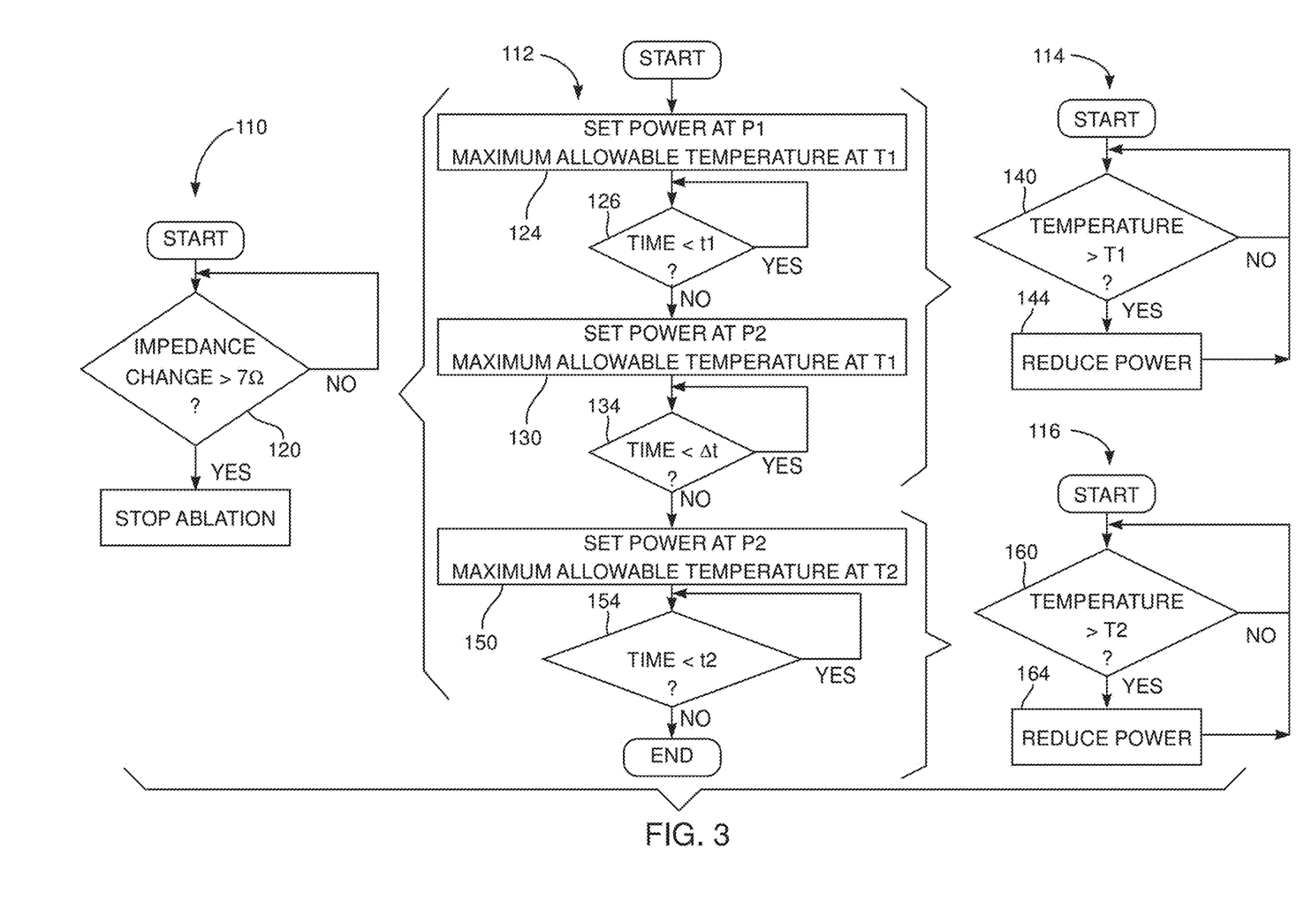
FIG. 3 shows flowcharts of steps performed during an ablation session of the procedure, according to an embodiment of the present invention.
Figure 4:
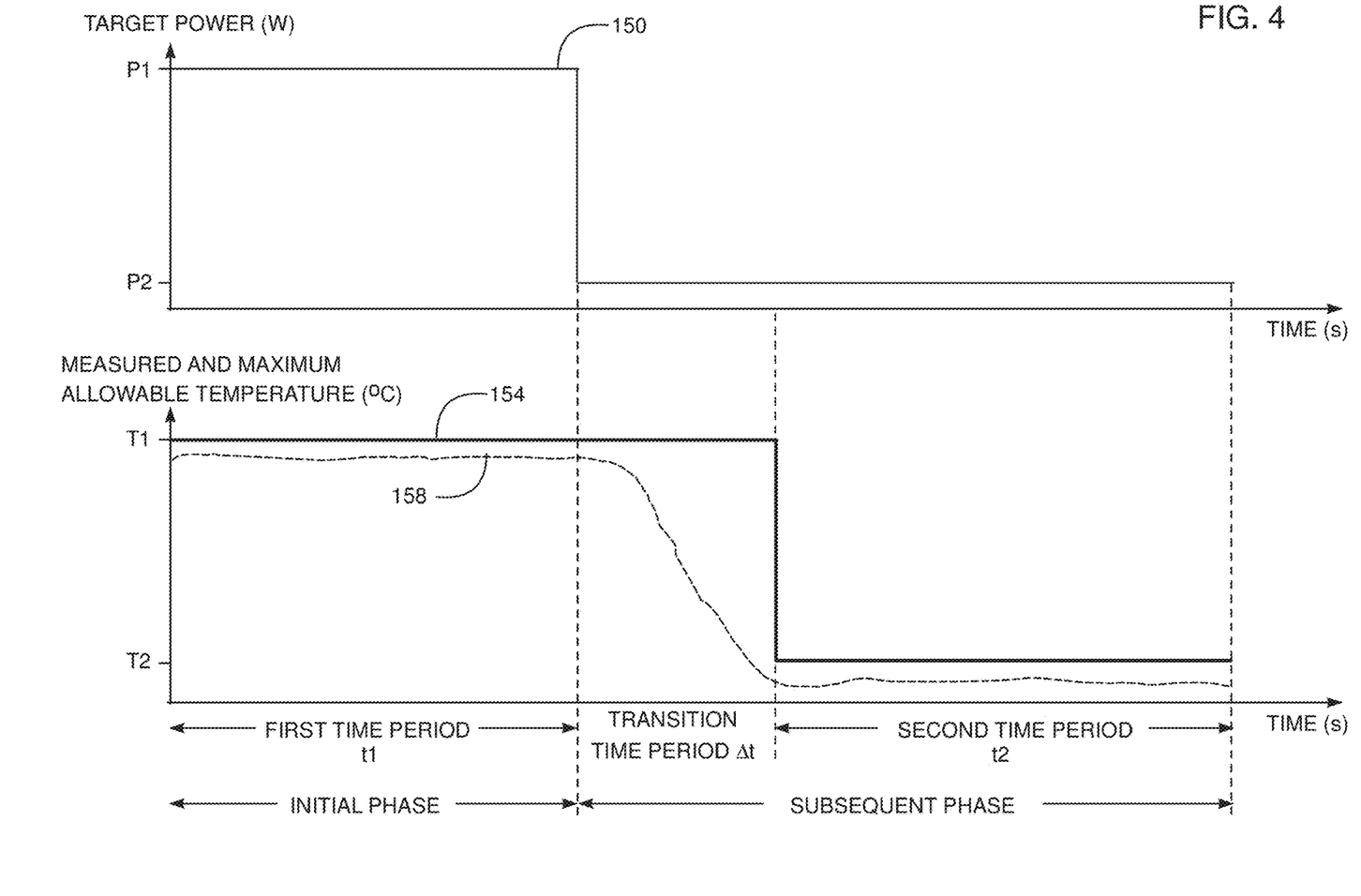
FIG. 4 shows schematic graphs illustrating the flowchart steps, according to an embodiment of the present invention.

FIG. 3 shows flowcharts 110, 112, 114, and 116 of steps performed in operation of apparatus 12 during an ablation session, and FIG. 4 shows schematic graphs illustrating steps of the flowcharts, according to an embodiment of the present invention. In an embodiment of the present invention, an ablation session comprises two time phases: an initial phase or first time period, during which a first target power and a first maximum allowable temperature applies. At the end of the initial phase, a subsequent phase begins during which a second target power applies.

The subsequent phase is divided into two time periods: a transition time period followed by a second time period. During the transition time period, after the end of the first time period, the first maximum allowable temperature applies. During the second time period a second maximum allowable temperature applies. The target powers within each time period are maximum RF powers which may be delivered by power control module 54.

Typically, prior to the ablation session, ranges for each of the variable parameters referred to above are set. In one embodiment the ranges are set as shown in Table I.

TABLE I

| Parameter | Range |
| --- | --- |
| First Target Power P1 | 70 W-100 W |
| Second Target Power P2 | 20 W-60 W |
| First maximum allowable temperature T1 | 55° C.-65° C. |
| Second maximum allowable temperature T2 | 40° C.-50° C. |
| First Time Period (during which First Target Power is operative) t1 | 1 s to 6 s |
| Transition Time Period (between end of First Time Period and time of change of maximum allowable temperature and during which First maximum allowable temperature and Second Target Power apply) Δt | 1 s to 2 s |
| Second Time Period (during which Second maximum allowable temperature T2 and Second Target Power apply) t2 | Up to 13 s |
| Irrigation rate | 8-45 ml/min |
| Allowable Force | 5 g-50 g |

At the beginning of an ablation session, physician 14 inserts probe 20 into a desired location in myocardium 16, using the tracking system incorporated into apparatus 12.

Prior to performing the ablation procedure, physician 14 selects values of the parameters listed in Table I that are to be used in the procedure, and uses controls 49 to provide the values to the system. Alternatively, the physician selects a predetermined set of the values of the parameters listed in Table I, typically by choosing a "recipe," comprising the values, from a group of such recipes. (The group of recipes is typically presented to the physician on screen 62 in the form of menus, from which the physician selects one.) The selected values typically depend on the depth of lesion it is desired to form by the procedure.

Table II below gives exemplary values of the parameters of Table I for forming a deep lesion of up to 6 mm depth.

TABLE II

| Parameter | Range |
| --- | --- |
| First Target Power P1 | 90 W |
| Second Target Power P2 | 50 W |
| First maximum allowable temperature T1 | 60° C. |
| Second maximum allowable temperature T2 | 47° C. |
| First Time Period (during which First Target Power is operative) t1 | 4 s |
| Transition Time Period (between end of First Time Period and time of change of maximum allowable temperature and during which First maximum allowable temperature and Second Target Power apply) Δt | 1 s |
| Second Time Period (during which Second maximum allowable temperature T2 and Second Target Power apply) t2 | 5 s |
| Irrigation rate | 8 ml/min |
| Allowable Force | 5 g-20 g |

During the whole of an ablation session, processor 46 implements the steps of flowcharts 110 and 112. As is explained in more detail below, during the first time period and the transition time period of the session the processor also implements the steps of flowchart 114, and during the second time period of the session the processor implements the steps of flowchart 116.

Referring to flowchart 110, which, as stated above, the processor implements (iteratively) during the whole of the ablation session, in a comparison step 120 the processor checks if the impedance to the power delivered by the ablation electrode changes by more than a preset value, herein assumed to be 7Ω. If the check returns negative, the comparison is repeated. If the check returns positive, the processor stops the ablation session.

Flowchart 112 comprises steps which are also implemented by the processor for the whole ablation session. In an initial step 124, the processor applies the selected values of first target power P1 and maximum allowable temperature T1 for the initial phase of the session. These values are maintained by the processor checking, in a comparison 126, if the time of ablation has not exceeded the first time period t1.

Once the first time period is exceeded, control proceeds to a change target power step 130, where the processor changes the target power to the second target power value P2 while keeping the maximum allowable temperature at T1. The processor maintains the values P2 and T1 for a transition time period Δt, by checking that the time has not exceeded Δt in a comparison 134.

While implementing steps 124-134 of flowchart 112, the processor also implements flowchart 114 and checks, in a comparison step 140, that the measured temperature does not exceed the maximum allowable temperature T1. If the temperature does exceed T1, the processor reduces the power to the ablation electrode, as described above, in a reduce power step 144.

A target power vs. time graph 150 (FIG. 4) shows that during the first time period, corresponding to times when step 124 and comparison 126 are operative, the target power is set at P1. The graph also shows that during the transition time period Δt, i.e., when comparison 134 is operative, the target power is reduced to P2.

A maximum allowable temperature vs. time graph 154, and a measured temperature vs. time graph 158 show that during the first time period the maximum allowable temperature is set at T1, and the measured temperature is less than this. The graphs also illustrate that during the transition time period Δt the maximum allowable temperature is maintained at T1, but the measured temperature falls, because of the reduction in target power to P2.

Returning to flowchart 112, when comparison 134 returns negative, i.e., when the transition time period Δt has completed, control proceeds to a change maximum allowable temperature step 150 wherein the target power is maintained at P2, but the maximum allowable temperature is reduced to T2. The processor retains these values, P2 and T2, during the second time period of ablation, i.e., for a second time period t2, by confirming that a comparison 154 returns positive. When comparison 154 returns negative, second time period t2 has completed, and the ablation procedure completes by the processor zeroing the power supplied to the ablation electrode.

While implementing steps 150 and 154 of flowchart 112, the processor also implements flowchart 116 and checks, in a comparison step 160, that the measured temperature does not exceed the maximum allowable temperature T2. If the temperature does exceed T2, the processor reduces the power to the ablation electrode in a reduce power step 164.

It will be appreciated that by incorporating the transition time period described above into ablation procedures, embodiments of the present invention overcome the non-linear tissue response vs. temperature properties of tissue. The transition time period allows for a gradual decrease of measured temperature while allowing the power generator to continue supplying power.

While the description above assumes that transducer 24A comprises an electrode which converts electrical power into heat used for ablation, it will be appreciated that other transducers may be used, with the description herein being altered, mutatis mutandis. For example, transducer 24A may comprise an ultrasonic transmitter, which converts electrical power into ultrasound, and the ultrasound is converted to heat. All such transducers are considered to be within the scope of the present invention.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus, comprising:
   a probe having a distal end comprising a temperature sensor and a transducer in contact with tissue in a body of a living subject;
   a power supply configured to deliver electrical power to the transducer, so as to ablate the tissue; and
   a controller, coupled to the power supply and to the probe, and configured:
   to receive a signal from the temperature sensor and in response to the signal to output an indication of a temperature of the tissue,
   during a first time period to activate the power supply to deliver no more than a first target power to the transducer so as to ablate the tissue, and to reduce the electrical power delivered to the transducer when a first maximum allowable temperature of the tissue is exceeded,
   during a transition time period immediately following the first time period, to activate the power supply to deliver no more than a second target power, less than the first target power, to the transducer so as to ablate the tissue, while reducing the delivered power when the first maximum allowable temperature of the tissue is exceeded, wherein during the transition time period the controller ensures that the first maximum allowable temperature is maintained while the power is reduced to the second power thereby providing for a gradual decrease of measured temperature, and
   during a second time period immediately following the transition time period, to activate the power supply to deliver no more than the second target power to the transducer, while reducing the delivered power when a second maximum allowable temperature, less than the first maximum allowable temperature, is exceeded.

2. The apparatus according to claim 1, wherein the transducer comprises one of an electrode or an ultrasonic transmitter.

3. The apparatus according to claim 1, wherein the electrical power comprises radiofrequency power.

4. The apparatus according to claim 1, wherein the controller is configured to deliver a first actual power less than the first target power in the first time period, and to deliver a second actual power less than the second target power in the transition time period and in the second time period.

5. The apparatus according to claim 1, wherein the transducer comprises an electrode, and wherein the power supply is configured to measure an impedance of the electrode during the first, transition, and second time periods, and to stop delivery of the electrical power if the impedance exceeds a pre-set value.

6. The apparatus according to claim 1, wherein the first target power is between 70 W and 100 W, and wherein the second target power is between 20 W and 60 W.

7. The apparatus according to claim 1, wherein the first time period is between 1 s and 6 s, the transition time period is between 1 s and 2 s, and the second time period is up to 13 s.

8. A method, comprising:
providing a probe having a distal end comprising a temperature sensor and a transducer that is configured to contact tissue in a body of a living subject;
delivering electrical power from a power supply to the transducer, so as to ablate the tissue;
receiving a signal from the temperature sensor and in response to the signal
outputting an indication of a temperature of the tissue;
during a first time period activating the power supply to deliver no more than a first target power to the transducer so as to ablate the tissue, and reducing the electrical power delivered to the transducer when a first maximum allowable temperature of the tissue is exceeded;
during a transition time period immediately following the first time period, activating the power supply to deliver no more than a second target power, less than the first target power, to the transducer so as to ablate the tissue, while reducing the delivered power when the first maximum allowable temperature of the tissue is exceeded, wherein during the transition time period the controller ensures that the first maximum allowable temperature is maintained while the power is reduced to the second power thereby providing for a gradual decrease of measured temperature; and
during a second time period immediately following the transition time period, activating the power supply to deliver no more than the second target power to the transducer, while reducing the delivered power when a second maximum allowable temperature, less than the first maximum allowable temperature, is exceeded.

9. The method according to claim 8, wherein the transducer comprises one of an electrode or an ultrasonic transmitter.

10. The method according to claim 8, wherein the electrical power comprises radiofrequency power.

11. The method according to claim 8, and comprising delivering a first actual power less than the first target power in the first time period, and delivering a second actual power less than the second target power in the transition time period and in the second time period.

12. The method according to claim 8, wherein the transducer comprises an electrode, the method further comprising measuring an impedance of the electrode during the first, transition, and second time periods, and stopping delivery of the electrical power if the impedance exceeds a pre-set value.

13. The method according to claim 8, wherein the first target power is between 70 W and 100 W, and wherein the second target power is between 20 W and 60 W.

14. The method according to claim 8, wherein the first time period is between 1 s and 6 s, the transition time period is between 1 s and 2 s, and the second time period is up to 13 s.

\* \* \* \* \*